(12) United States Patent
Harper

(10) Patent No.: US 10,152,791 B2
(45) Date of Patent: *Dec. 11, 2018

(54) SYSTEM COMBINING AUTOMATED SEARCHES OF RADIOLOGIC IMAGES, ACCESSION NUMBER ASSIGNMENT, AND INTERFACILITY PEER REVIEW

(71) Applicant: Derrick K. Harper, Huntington Woods, MI (US)

(72) Inventor: Derrick K. Harper, Huntington Woods, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,800

(22) Filed: Sep. 1, 2017

(65) Prior Publication Data

US 2018/0025494 A1    Jan. 25, 2018

Related U.S. Application Data

(63) Continuation of application No. 14/878,179, filed on Oct. 8, 2015, now Pat. No. 9,786,051.

(Continued)

(51) Int. Cl.
*G06K 9/00* (2006.01)
*G06F 17/30* (2006.01)
(Continued)

(52) U.S. Cl.
CPC ........ *G06T 7/0014* (2013.01); *G06F 17/3028* (2013.01); *G06F 17/30064* (2013.01);
(Continued)

(58) Field of Classification Search
USPC ....... 382/100, 128–133, 155, 181, 190, 206, 382/209, 219, 224, 232, 254, 274, 276,
(Continued)

(56) References Cited

U.S. PATENT DOCUMENTS 6,151,581 A    11/2000   Kraftson et al.
6,175,354 B1   1/2001    Blissett et al.
(Continued)

FOREIGN PATENT DOCUMENTS

WO    2001035310 A    5/2001

OTHER PUBLICATIONS

Softek Solutions, Inc., ActKnowledge—Close the communication loop on incidental, critical and urgent findings, Brochure, 2011 copyright date, pp. 1-8, U.S.
(Continued)

*Primary Examiner* — Seyed Azarian
(74) *Attorney, Agent, or Firm* — Gregory L. Ozga; Warn Partners, P.C.

(57) ABSTRACT

A system that helps facilitate the creation of more comprehensive official radiological reports by remotely accessing a patient's prior outside imaging studies along with official radiological reports through a cloud server for comparison to current studies performed at a medical institute. The system includes universal interface software that will allow for previous patient studies to be automatically pulled for direct comparison by using advanced automatic tagging techniques. Additionally the universal interface software allows for more efficient accession number assignment when official second opinions are requested, and a means for interfacility peer review.

12 Claims, 8 Drawing Sheets

Related U.S. Application Data

(60) Provisional application No. 62/151,521, filed on Apr. 23, 2015.

(51) Int. Cl.
  *G06T 7/00* (2017.01)
  *G06F 19/00* (2018.01)
(52) U.S. Cl.
  CPC ...... *G06F 17/30268* (2013.01); *G06F 19/321* (2013.01); *G06T 2207/10116* (2013.01)
(58) Field of Classification Search
  USPC ........ 382/285–295, 305, 312; 707/709, 723; 378/4, 21
  See application file for complete search history.

(56) References Cited

U.S. PATENT DOCUMENTS

| | | | |
|---|---|---|---|
| 6,694,984 B2 | 2/2004 | Habib | |
| 7,016,952 B2 | 3/2006 | Mullen et al. | |
| 7,519,209 B2 | 4/2009 | Dawant et al. | |
| 7,979,383 B2 | 7/2011 | Heilbrunn et al. | |
| 8,032,398 B1 | 10/2011 | Kelly et al. | |
| 8,156,202 B2 | 4/2012 | Wallberg | |
| 8,175,354 B2 | 5/2012 | Liang et al. | |
| 8,180,783 B1* | 5/2012 | Fletcher | G06F 17/30684 707/723 |
| 8,285,703 B1* | 10/2012 | Wagers | G06F 17/30011 707/709 |
| 8,355,553 B2 | 1/2013 | Fidrich et al. | |
| 8,358,818 B2 | 1/2013 | Miga et al. | |
| 8,489,414 B2 | 7/2013 | McEachern | |
| 8,533,006 B2 | 9/2013 | Manning et al. | |
| 8,553,965 B2* | 10/2013 | Zhao | G06F 9/5072 382/131 |
| 8,571,280 B2* | 10/2013 | Mathew | G06F 19/3418 382/128 |
| 9,223,836 B1* | 12/2015 | Fletcher | G06F 17/30684 |
| 2004/0117215 A1 | 6/2004 | Marchosky | |
| 2004/0141661 A1 | 7/2004 | Hanna et al. | |
| 2004/0146221 A1 | 7/2004 | Siegel et al. | |
| 2004/0243448 A1 | 12/2004 | Shoji et al. | |
| 2005/0027570 A1 | 2/2005 | Maier et al. | |
| 2005/0244082 A1 | 11/2005 | Yamatake | |
| 2010/0241455 A1 | 9/2010 | Gilbert et al. | |
| 2011/0110568 A1* | 5/2011 | Vesper | G06F 19/321 382/128 |
| 2011/0153351 A1 | 6/2011 | Vesper et al. | |
| 2012/0143618 A1 | 6/2012 | Gilbert et al. | |
| 2013/0110537 A1 | 5/2013 | Smith | |
| 2015/0178458 A1 | 6/2015 | Pellinat et al. | |

OTHER PUBLICATIONS

Softek Solutions, Inc., Softek Illuminate—Find your future in the history, Brochure, 2014 copyright date, pp. 1-8, U.S.

Softek Solutions, Inc., Illuminate InSight, Brochure, 2014 copyright date, p. 1, U.S.

Softek Solutions, Inc., Illuminate Analytics, Brochure, 2014 copyright date, p. 1, U.S.

Softek Solutions, Inc., Illuminate PatientView, Brochure, 2014 copyright date, p. 1, U.S.

\* cited by examiner

SYSTEM COMBINING AUTOMATED SEARCHES OF RADIOLOGIC IMAGES, ACCESSION NUMBER ASSIGNMENT, AND INTERFACILITY PEER REVIEW

CROSS-REFERENCE TO RELATED APPLICATIONS

This application claims the benefit of U.S. Provisional Application No. 62/151,521, filed Apr. 23, 2015.

FIELD OF THE INVENTION

The present invention relates to a system for creating more comprehensive radiologic reports by accessing prior patient studies via a cloud system, more efficient methods for accession number assignment, and interfacility peer review.

BACKGROUND OF THE INVENTION

One of the most important diagnostic skills that radiologists acquire during their training is learning the value of prior comparisons when interpreting imaging studies in order to generate useful reports for the referring clinical service. Unfortunately past radiological images are often not available at the medical institute because patients often have studies done at several different medical institutes. When past images are not available recommendations may be made for further unnecessary imaging studies or procedures leading to increased cost, procedure related complications and inaccurate diagnoses. Unnecessary imaging studies and procedures are less likely to occur at a large integrated health system where the patient has a significant image history accessible to the radiologist through the health system's PACS. However, when a patient has had multiple imaging studies at multiple outside medical institutes, it is not always possible to be aware of what past studies and images have been taken, which often relies on the images being placed on a digital imaging storage media, such as CDs or radiological film and then mailed to the requesting facility or delivered by hand, potentially delaying critical diagnoses. There is a need to build patient imaging libraries across medical institutes. There is also a need to tag the images in the patient library that allows radiologists to quickly locate and access past images for comparison with current images.

Cloud server technology has provided a solution to the problem of centralizing a patient's imaging studies, making them more easily accessible from remote sites. The number of imaging studies being performed continues to increase exponentially. This is compounded by the fact that patients are living longer, but are not necessarily healthier and the Affordable Care Act has made healthcare more accessible. There is a need for more efficient means of searching through libraries of imaging studies in the generation of more complete radiological reports especially when outside studies are being accessed through cloud for comparison.

As medical facilities become more integrated through the use of cloud technology, interfacility peer review could conceivably become a requirement by the American College of Radiology and the Joint Commission on Accreditation of Healthcare Organizations. Peer review is most commonly used for assessing performance in terms of diagnostic ability among radiologists. Ultimately the goal of peer review is to reduce interpretive errors and improve care. Currently the American College of Radiology and the Joint Commission on Accreditation of Healthcare Organizations requires that medical facilities participate in peer review to maintain accreditation. A radiologist at their institution reviews a set number of imaging studies interpreted by his or her peers, and for each reviewed imaging study a case review submission page is generated which will have options of concur, disagree (difficult diagnosis), disagree (diagnosis should be made most of the time), disagree (diagnosis should be made every time), and a comments section for explaining the findings. Although there are no current requirements for peer review of outside interpretations, conceivably, there will be a need for radiologists to peer review colleagues from outside facilities.

An additional problem that arises with the decentralization of sharing radiological images using the traditional methods of transferring past images on a storage medium is often referred to as a "curbside consultation." The term "curbside consultation" refers to an unofficial consultation obtained by healthcare professionals usually from another health care professional, such as a radiologist on staff at the medical institute. Curbside consultations with regard to outside imaging studies are often requested by physicians in one department, such as an emergency room physician or surgeon, to a radiologist on staff. In such scenarios radiologists are often requested to provide a quick read of the diagnostic image without creating a documented report. This can be problematic for radiologists because the requesting physician will then place notes in the patient's file concerning what the radiologist told them. This can create several problems. First, the only written record of the radiologist is the hearsay opinion of what the requesting physician heard, which may or may not be entirely accurate. Also the requesting physician does not have any written record to refer back to in case they misunderstood the radiologist. This creates a liability burden for the radiologist. Second, the radiologist does not receive any compensation for the "curbside consultation" which is not equitable given the degree of malpractice liability that can arise from a curbside consultation. Third, for the time spent on such consults the radiologist will not receive the appropriate relative value units or RVUs which are used to measure individual physician productivity. However, curbside consultations can be very important, especially in emergency situations where time is of the essence. The rate limiting step in creating an official radiologic report of an outside imaging study is the assignment of accession numbers. Current methods for accession number assignment as it relates to curbside consultation are inefficient in that ancillary staff coordination is required which can delay critical diagnoses. There is a need for more efficient means of assigning accession numbers to outside imaging studies so official radiologic reports can be created during curbside consultation.

SUMMARY OF THE INVENTION

The present invention relates to a system for cloud-based radiological image comparisons and a method of generating reports therefrom. The system includes the step of providing universal interface software for standardizing all information uploaded to a cloud server accessible through internet via a secure connection. The cloud server is provided and operates the universal interface software having at least one patient library located on the cloud server. The at least one patient library is for a specific patient and is used for storing at least one previous patient study prepared by a first medical institute as part of the at least one patient library. The at least one previous patient study includes written patient information, including patient name and date of study and is created using the universal interface software in order to ensure compatibility with systems accessing the cloud server.

The at least one previous patient study also includes at least one patient diagnostic image, a written report pertaining to the at least one patient diagnostic image, and at least one image procedure tag pertaining to how the diagnostic image was obtained. There is also at least one image view tag pertaining to the viewpoint of the at least one patient diagnostic image, an automatically assigned accession number, and an automatically assigned universal medical record number associated with the at least one previous patient study. The at least one previous patient study also contains automatically assigned anatomical sub-tags. The universal interface software is programmed to assign the anatomical sub-tags based on the at least one image procedure tag and the at least one image view tag. The universal interface software is also programmed to perform a keyword tagging step where the universal interface software in combination with a computer reads a written report associated with a patient study and then generates keyword tags by recognizing anatomical language in the written report of the comparison patient study.

The system further includes a step of providing a second medical institute operating the universal interface software, which is capable of communicating with the cloud server. The second medical institute has at least one radiological diagnostic image device, at least one workstation, a picture archiving and communication system for storing patient images and reports created or downloaded for review at the second medical institute. At the second medical institute at least one comparison patient diagnostic image is created using the at least one radiological image device. The at least one comparison patient diagnostic image is then uploaded to the picture archiving and communication system at the second medical institute.

Next the step of using the at least one workstation at the second medical institute takes place where the at least one workstation is used to access the at least one comparison patient diagnostic image located on the picture archiving and communication system at the second medical institute. The step of tagging the at least one patient comparison diagnostic image takes place by a user of the at least one workstation using a graphical user interface and the universal interface software to select at least one image procedure tag pertaining to the type of image and how it was obtained. Next a user using the graphical user interface selects at least one image view tag pertaining to the viewpoint of the at least one patient diagnostic image. The universal interface software automatically assigns anatomical sub-tags, an accession number, and a universal medical record number to the comparison patient study. The universal interface software is programmed to assign the anatomical sub-tags based on the at least one image procedure tag and the at least one image view tag.

Next a user of the at least one workstation performs the step of reviewing the at least one patient comparison diagnostic image and identifies an abnormality in the at least one comparison patient diagnostic image that requires further investigation.

Next is the step of accessing the at least one patient library on the cloud server using the at least one workstation being controlled by a user. The universal interface software on the at least one workstation at the second medical institute sends a request to the cloud server to search the at least one patient library for any at least one patient diagnostic image containing the same anatomical sub-tags as the at least one comparison patient diagnostic image. Next at least one previous patient study that includes the at least one patient diagnostic image matching the request is downloaded from the cloud server to the picture archiving and communication system of the second medical institute. The universal interface software on the at least one workstation at the second medical institute automatically links the universal medical record number from the previous patient study to the universal medical record number of the comparison patient study.

Next a comparison patient study is created with a written report comparing the at least one comparison patient diagnostic image and the at least one previous patient study downloaded from the cloud server. During this step the at least one patient diagnostic image from the at least one previous patient study is downloaded from the cloud server and the at least one comparison patient diagnostic image are organized into a timeline on the at least one workstation at the second medical institute. Next the at least one patient diagnostic image from the previous patient study and the at least one comparison patient diagnostic image are reviewed in a side-by-side comparison to conduct further investigation of the abnormality noted in the at least one comparison patient diagnostic image. The comparison patient study includes a review of the abnormality noted in the at least one comparison patient diagnostic image and the presence or absence of an abnormality in the at least one previous patient study downloaded from the cloud server. Lastly the step of uploading the comparison patient study from the second medical institute to the cloud server and saving the comparison patient study to the at least one patient library on the cloud server takes place.

Areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
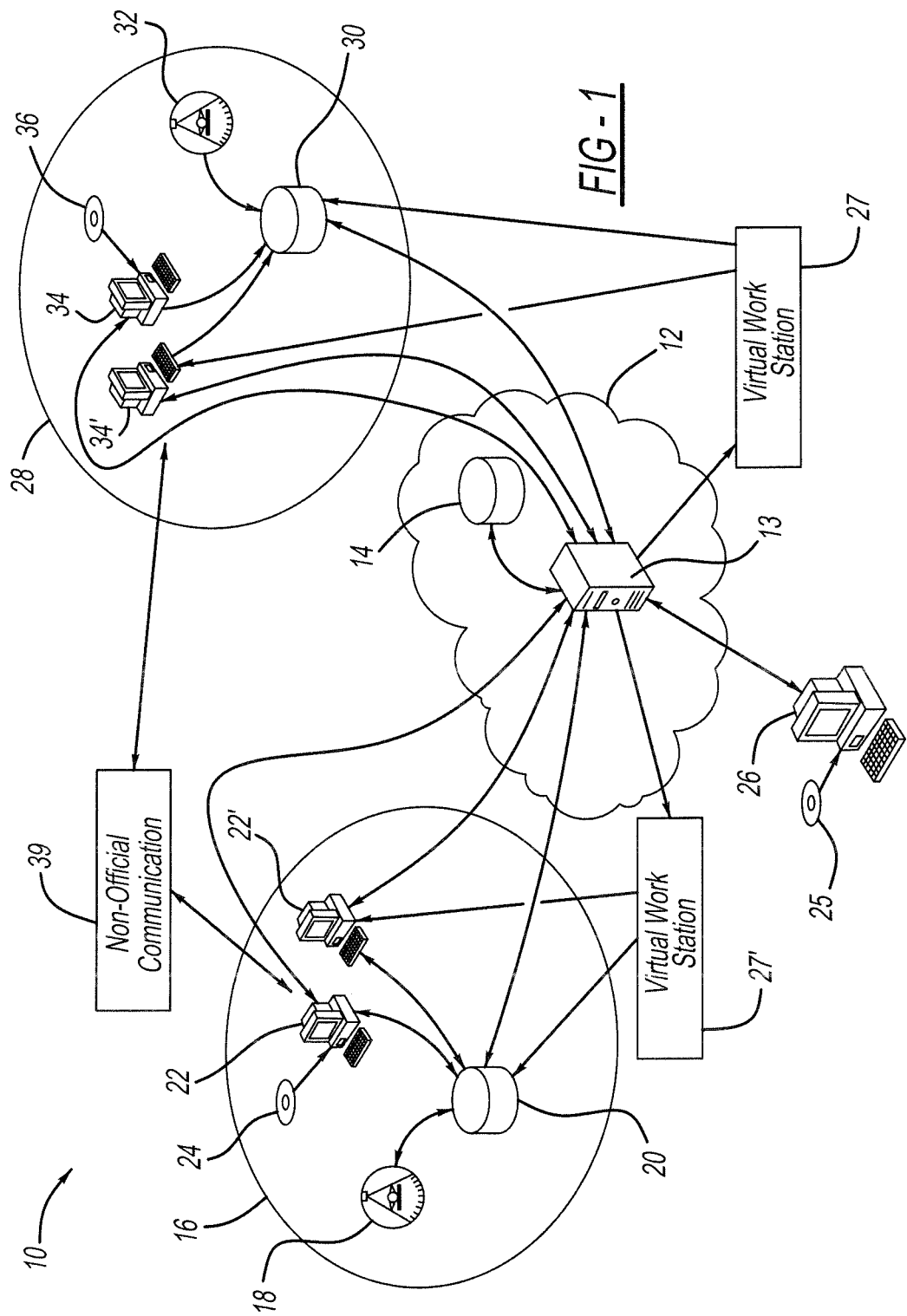
FIG. 1 is a schematic diagram of a system for cloud based radiological image comparisons and method of generating reports.

The following description of the preferred embodiment(s) is merely exemplary in nature and is in no way intended to limit the invention, its application, or uses.

Throughout this specification the following terms are used, which are defined as follows. The term "medical institute", whether called "first medical institute", "second medical institute" or just "medical institute" is used to refer to any type of organization or individual that prepares patient studies or uploads patient diagnostic images and includes individual physicians, physician practices, hospitals, research institutes, or any other individual or organization concerned with preparing and uploading information into the at least one patient library, associated with a specific patient.

The term "patient study" or "patient studies" also including the terms "previous patient study", "previous patient studies", "comparison patient study", "comparison patient studies", "manual patient study" and "manual patient studies" include written patient information including medical record numbers, patient name and date of study and one or more patient diagnostic images; each of these terms may or may not include a written report pertaining to the patient diagnostic images, one or more image procedure tags pertain to nature of the image and how it was obtained, one or more of view tags pertaining to the viewpoint of the patient diagnostic images, medical record numbers and automatically assigned anatomical sub-tags and keyword tags. For example, a "manual patient study", which is described as being obtained from a compact disc, might not contain any other information than the medical record number, patient name and date of study along with just diagnostic images and no other written reports. The term "patient library" refers to a group of one or more patient study files that pertain to a specific individual patient.

The terms "patient diagnostic image", "patient diagnostic images", "radiological diagnostic image" and "radiological diagnostic images" are defined herein to include one or more diagnostic images prepared from various diagnostic equipment, including but not limited to x-rays, magnetic resonance imaging (MRI) data or images, computerized tomography (CT) scans, positron emission tomography (PET), mammograms (MG), computed radiography (CR), ultrasound data or images or any other medical diagnostic images or data, etc. The images can be taken from multiple medical diagnostics devices and it is also possible that they are taken from different views or comprise a series of images or data blocks.

The term "picture archiving and communication system" will at times be referred to by the acronym PACS and is defined to be a server or mainframe located at one of the medical institutes for localized storage of at least one patient diagnostic image and patient study files at a medical institute.

The term "accession number" is defined to be a unique identifier number assigned to a specific order or set of diagnostic images that become part of a patient study and are subsequently saved to the PACS and or cloud server. The accession number is used for generating bills for services as well as cataloging the patient study and associated images.

The term "medical record number" includes the term "universal medical record number" and is defined to be a unique number given to a patient to identify that patient out of a group of patients.

Referring now to all the figures, with particular reference to FIG. 1 shows a system 10 overview for preparing and uploading radiologic diagnostic images to a cloud server 12. The cloud server 12 includes a mainframe 13 and data storage unit 14, which can be separate units or a single unit. Both the mainframe 13 and data storage unit 14 are hereafter collectively referred to as the cloud server. The data storage unit 14 is the portion of the cloud server 12 that stores patient libraries that pertain to a specific patient. Each patient library includes at least one previous patient study that includes written patient information including automatically assigned medical record number, accession number, patient's name, date of the study, at least one patient diagnostic image, and possibly a written report pertaining to the at least one patient diagnostic image, at least one image procedure tag, at least one image view tag, and automatically assigned anatomical sub-tags and keyword tags.

Each patient study located on the cloud server 12 is uploaded to the cloud server 12 from a couple of different sources. A first source is a first medical institute 16 capable of uploading and downloading patient studies to the cloud server 12. In order to properly upload the patient study the first medical institute 16 uses pre-loaded universal interface software operating on a picture archiving and communication system (PACS) 20 or on the workstation 22, 22'. It is also within the scope of this invention for the cloud server 12 to provide a virtual workstation 27' to the first medical institute 16 either through the PACS 20 or directly to the workstation 22, 22' by uploading a web based portal that includes the universal interface software. The use of the universal interface software and the virtual work station 27' ensures that any data including patient studies uploaded from the first medical institute 16 to the cloud server 12 are uploaded using a universal interface software format that will be consistent across the system 10.

The first medical institute 16 has one or more radiological diagnostic image devices 18 that are used to create images and upload them to a picture archiving and communication system 20 located at the first medical institute 16. Within the first medical institute 16 there are workstations 22, 22' that communicate with the PACS 20. The workstations 22, 22' are able to retrieve the images stored on the PACS 20, which were taken using the radiological diagnostic image devices 18. It is also within the scope of this invention for the workstations 22, 22' to communicate directly with the cloud server 12, which could eliminate the need to have a PACS 20 at the first medical institute 16.

Another source of diagnostic image data is provided by a compact disc (CD) 24 that is read by the workstation 22, 22' and the images from the compact disc 24 are uploaded from the workstation 22, 22' to the picture archiving and communication system 20 or directly to the cloud server 12. The workstation 22, 22' is used to prepare or analyze the diagnostic images from the diagnostic image device 18 or the images from the compact disc 24, into a patient study file created on the workstation 22, 22', that will include a written report pertaining to the at least one patient diagnostic image that was reviewed at the workstation 22, 22'. The workstation 22, 22' is used to command the PACS 20 to upload the previous patient study file to the cloud server 12 using a secure internet connection or the workstation 22, 22' can be configured to directly upload the previous patient study to the cloud server 12.

FIG. 1 also shows another source of diagnostic image data or patient study data where a compact disc (CD) 25 is uploaded onto the cloud server 12 directly by a patient at his or her personal computer 26. The patient can be granted access to his or her patient library located on the cloud server 12 using a personalized login and password associated with their universal medical record number that is automatically assigned to their patient library using the universal interface software located on the cloud server 12. In order to properly upload the patient study from the compact disc 25 the cloud server 12 provides a virtual workstation 27 on the personal computer 26 by uploading a web based portal that includes the universal interface software, in order to ensure that any data uploaded from the compact disc 25 from the personal computer 26 to the cloud server 12 is uploaded using a universal software format. This will ensure that any data including patient studies and diagnostic images uploaded from the personal computer 26 will be in a format that will be accessible and readable by any medical institute that uploads the information from the cloud server 12.

It is also within the scope of this invention for the personal computer 26 to not be operated by a patient, but rather by a physician or some other medical professional from his or her home or office computer. It is sometimes necessary for physicians to have remote access to patient studies. One feature of the present invention is that having patient studies located on the cloud server 12 allows a physician quick remote access to a patient study file from the server 12, especially when the physician is unable to see a patient in person at a medical institute. Such ability will allow a physician to be able to provide better patient care and also help other medical personnel who have immediate access to the patient.

Another source of diagnostic image data and patient studies is a second medical institute 28 having its own picture archiving and communication system 30 (PACS) capable of communicating with the cloud server 12 in order to upload and download patient studies to and from a patient library located on the data storage device 14 connected to the cloud server 12. The second medical institute 28 also has radiological diagnostic image devices 32 connected to the picture archiving and communication system 30 of the second medical institute 28. Multiple workstations 34, 34' are connected to the PACS 30 of the second medical institute 28. Workstations 34, 34' access patient diagnostic images stored on the PACS 30, which were created from the radiological diagnostic image devices 32 at the second medical institute 28. The images can also be uploaded to the cloud server 12 using the workstations 34, 34'. The workstations 34, 34' are also used to review and upload patient study files and manual patient diagnostic images from a compact disc 36. When the manual patient studies are uploaded from the compact disc 36 using the workstations 34, 34' at step 35(FIG. 8A) the manual diagnostic images are automatically uploaded to the PACS 30 and are immediately assigned a medical record number and accession number either at the individual workstations 34, 34' or at the PACS 30. This eliminates the need to involve ancillary staff for accession number assignment when a radiologist at workstation 34, 34' or PACS 30 is approached by an emergency room physician, surgeon, etc., for a curbside consultation regarding the manual patient diagnostic images from compact disc 36. The manual patient studies are then uploaded from the workstation 34, 34' to the PACS 30 of the second medical institute 28 and can also be uploaded to a patient library located at the cloud server 12. This allows for comparison patient studies to be prepared based off of diagnostic images brought in from the compact disc 36, which can subsequently be uploaded to the PACS 30 and cloud server 12 from the second medical institute 28.

It is also within the scope of this invention for the cloud server 12 to provide a virtual workstation 27 to the second medical institute 28 either through the PACS 30 or directly to the workstation 34, 34' by uploading a web based software component that includes the universal interface software. The use of the universal interface software and the virtual work station 27 ensures that any data including patient studies and diagnostic images are uploaded from the second medical institute 28 to the cloud server 12 using a universal software format. Additionally any data uploaded from the compact disc 36 at the second medical institute 28 will also be uploaded to the cloud server 12 using the universal interface software.

During review of the manual patient diagnostic images as part of a second opinion or the diagnostic images created at the second medical institute 28, abnormalities in the images might be noticed. Abnormalities are generally something in the diagnostic image that warrants further investigation or study and can include suspected tumors or simply be the result of the radiological image such as a shadow or unclear image, all of which might require further investigation. If an abnormality is noticed a physician at the workstation 34, 34' may begin to create a comparison patient study where the physician will designate the patient diagnostic image from the second medical institute 28 as a comparison patient diagnostic image. The physician will then use the workstation 34, 34' to query the cloud server 12 either directly or through the PACS 30 of the second medical institute 28. During the query process the physician will request the server to search the patient library located on the cloud server 12 and request the cloud server 12 to search the patient library for any patient diagnostic image containing the same image view tags, image procedure tags, anatomical sub-tags and keyword tags as the comparison patient diagnostic image and then download the previous patient study which includes the matching diagnostic image from the cloud server 12 to the PACS 30 of the second medical institute 28.

Another aspect of the invention allows a physician or user of the workstation 34, 34' at the second medical institute 28 to conduct non-official communication 39 to a physician at a workstation 22, 22' located at the first medical institute 16. The non-official communication 39 does not get recorded in the cloud server 12. Non-official communication 39 can include email messages and is intended to be directed more toward social discourse either about the diagnostic images for the patient or regarding other non-medical matters. The purpose of non-official communication 39 is to provide physicians with a less formal avenue for communication in instances where the circumstances surrounding a particular case do not warrant an official peer review.

While FIG. 1 shows two medical institutes 16, 28 and a single personal computer 26 and communication with the cloud server 12, it is within the scope of this invention for a greater or lesser number of personal computers and medical institutes to be in communication with the cloud server 12.

Figures 2, 3:
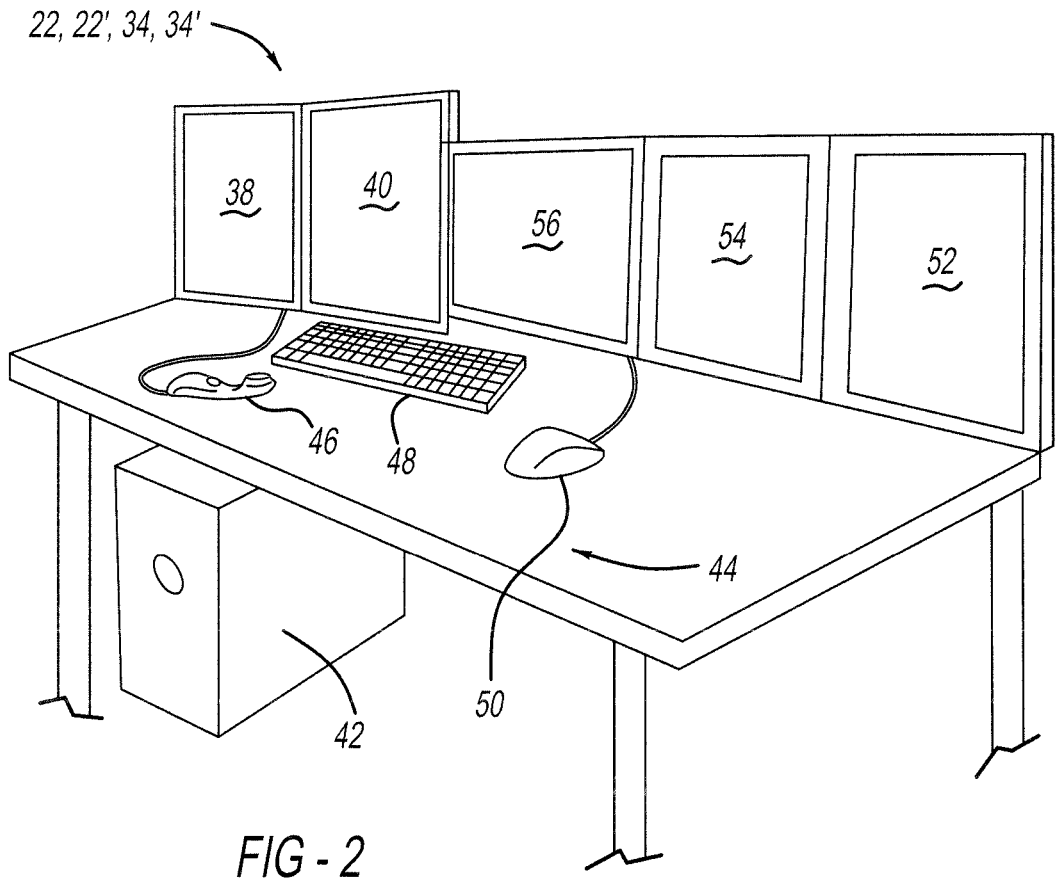
FIG. 2 is a schematic diagram showing a workstation at a medical institute in accordance with the present invention.
FIG. 3 is a screenshot of a work list monitor.

Referring now to FIG. 2, a layout of the workstation 34, 34' is shown and described. The workstation 34, 34' is identical to the workstation 22, 22' at the first medical institute 16. Therefore the description of the workstation 34, 34' described in FIG. 2 will also apply to the workstation 22, 22' at the first medical institute 16. Each workstation 22, 22', 34, 34', includes a first image monitor 38 and second image monitor 40 that are connected to a tower 42 which is a high-performance computer that communicates with the respective PACS 20, 30. The tower 42 is also used to communicate with the cloud server 12, either through the PACS 20, 30 or directly with the cloud server through a secure internet connection.

The first image monitor 38 and second image monitor 40 are high resolution monitors having at least 3 megapixel resolution or above and the first image monitor 38 and second image monitor 40 are typically organized or arranged in a side by side manner in order to assist the physician in comparing images as well as being able to scroll through a list of images or studies that are organized on a timeline that is discussed below in greater detail.

The workstation 22, 22', 34, 34' also includes various interface devices 44 which include a dictaphone 46 that allows for a user of the workstation to dictate written reports, a keyboard 48 used for typing inputs, and a mouse 50 that is used to control a graphical user interface that moves between the various monitors of the workstation. The workstation 22, 22', 34, 34' also includes a voice recognition monitor 52 that is connected to and receives inputs from the tower 42 and is used to allow a physician to use or control the operation and inputs received from the dictaphone 46 and other various interface devices 44 in order to prepare a written report. During preparation of a written report the physician can view the voice recognition monitor 52 and see the written report that he or she is dictating and can also manually input text using the keyboard 48 and options from the mouse 50. In an alternate embodiment of the invention, the voice recognition monitor 52 is also where a physician can use the mouse 50 and its graphical user interface to select and tag various images displayed on the first image monitor 38 and second image monitor 40. The tagging of the images are discussed in greater detail below. However it is within the scope of this invention for the steps of tagging and preparing a written report to be conducted directly on the first image monitor 38 or second image monitor 40 and not have a voice recognition monitor 52.

The workstation 22, 22', 34, 34' also includes a work list monitor 54 connected to the tower 42 and a cloud monitor 56 connected to the tower 42. Referring now to FIG. 3 a sample screenshot of the work list monitor 54 is shown. The worklist monitor 54 displays the current list of diagnostic images recently prepared at the medical institute that need to be reviewed by a physician so that a formal written report and patient study can be prepared. The information on the work list monitor 54 includes information pertaining to the patient's name and the list of the various diagnostic images contained on the PACS 20, 30 that are waiting to be reviewed.

The cloud monitor 56 displays information obtained from the cloud server 12. The cloud monitor 56 can be used to show or confirm that patient studies have been uploaded to the cloud server or a physician may check the cloud server 12 to identify and download the previous patient studies from other medical institutes. Essentially the cloud monitor 56 is used to interface with the cloud server 12 so that a physician can send commands from the medical institute to the cloud server 12 in accordance with various aspects of the present invention.

The system 10 and its various components, including the workstations 22, 22', 34, 34' provide many different benefits such as allowing for patient study reports, including diagnostic images to be uploaded to the cloud server 12 where they can then be accessed by other medical institutes. The features of the system 10 and the method of operating the system 10 allow for the patient studies to be uploaded using the universal interface software to ensure that the diagnostic images and patient studies have a consistent format that is compatible across the various medical institutes. Additionally the system 10 and method allows for comparison patient studies to be conducted by examining previously uploaded patient studies and diagnostic images, thus saving time, improving patient care and eliminating needless additional studies since abnormalities or other areas of further investigation can be checked by reviewing the patient's previous studies located on the cloud server 12. Another benefit of the present invention is that the system 10 and its methodology allows for peer review and non-official communication to be conducted between physicians at different medical institutes, which encourages the sharing of information and communication between physicians with the common goal of providing better patient care.

Figure 7:
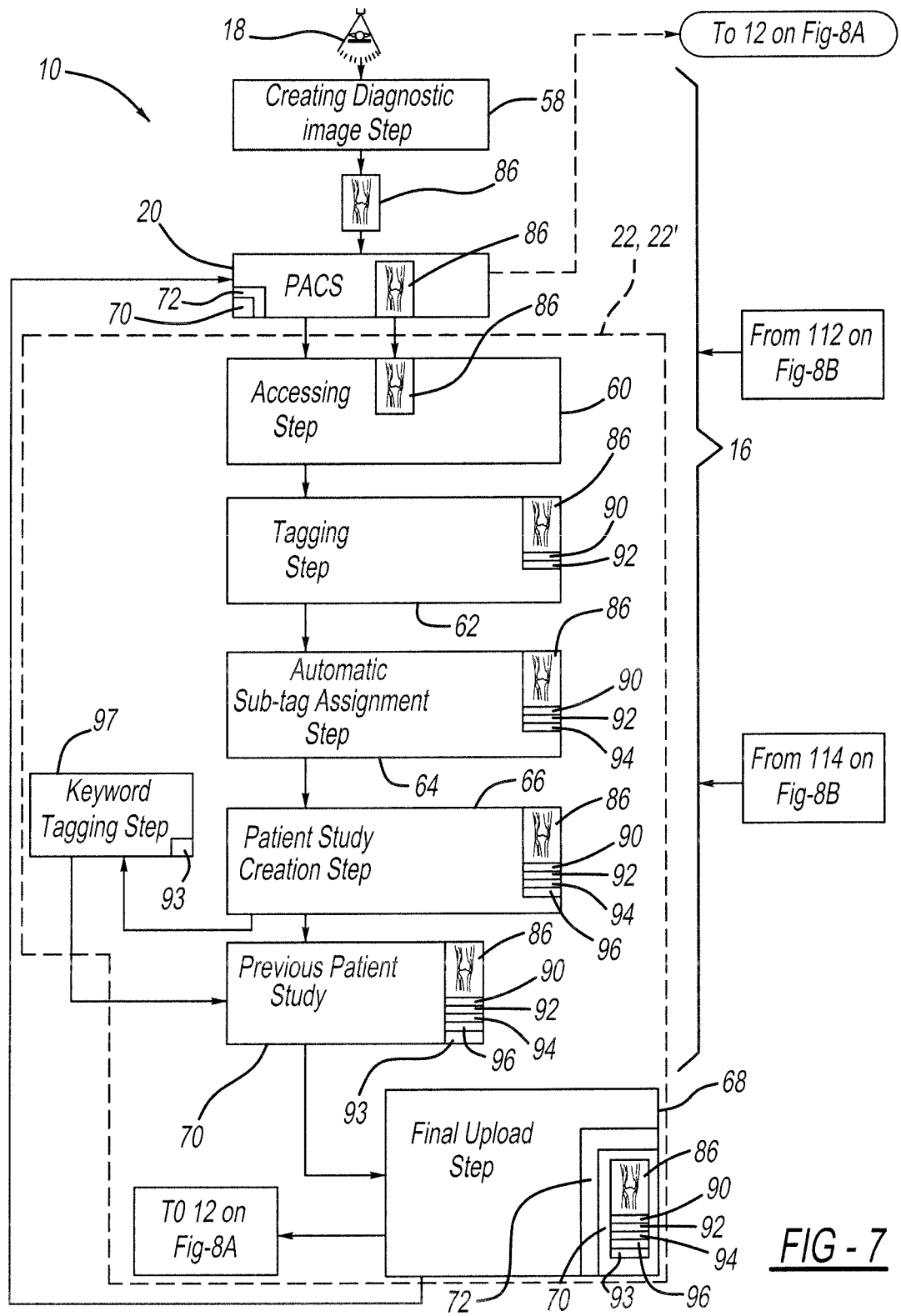
FIG. 7 is a portion of a flow chart showing the various steps of the method of operating the system in accordance with the present invention.
Figure 8A:
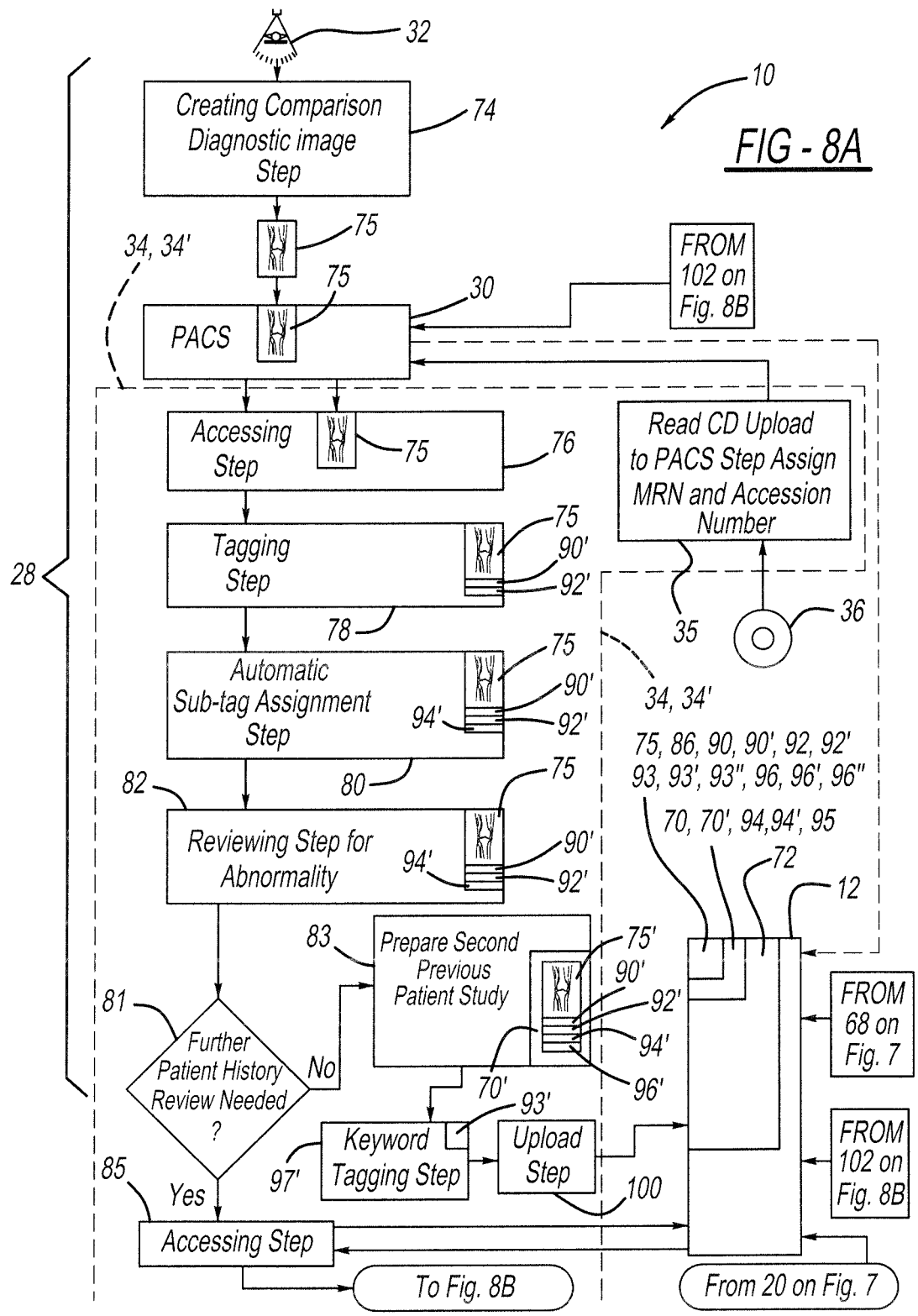
FIG. 8*a* is a portion of a flow chart showing the various steps of the method of operating the system in accordance with the present invention.
Figure 8B:
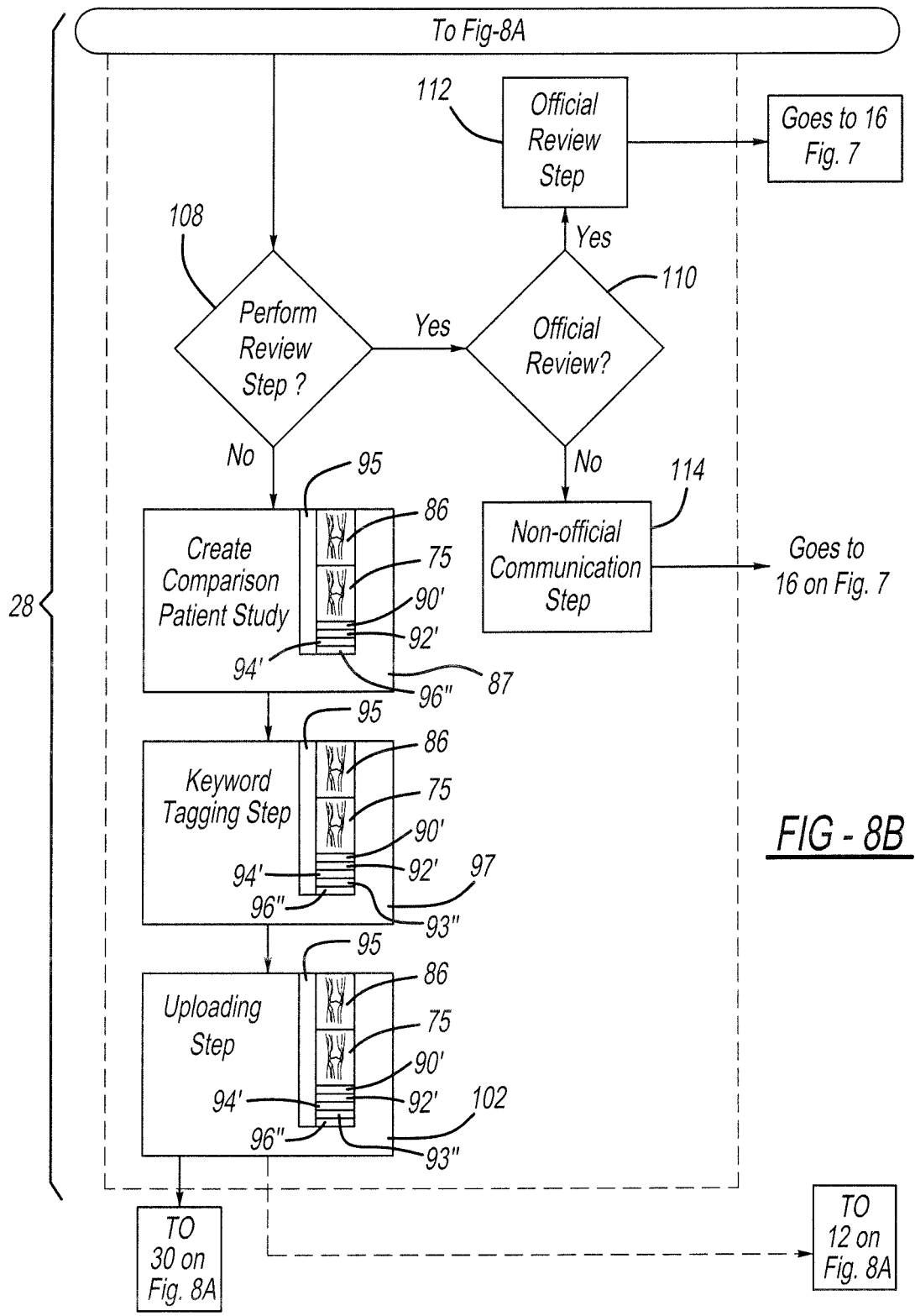
FIG. 8*b* is a portion of a flow chart showing the various steps of the method of operating the system in accordance with the present invention.

Referring now to FIGS. 7, 8A, and 8B are flowcharts of a method for using the system 10 in order to perform a comparison patient study in accordance with one aspect of the present invention. During such a method at a creating diagnostic image step 58 a physician or technician at the first medical institute 16 creates at least one patient diagnostic image 86 of a patient using one of the radiological diagnostic imaging devices 18. Typically a patient study will involve several images being taken, therefore it is within the scope of this invention for more than one diagnostic image to be prepared. The patient diagnostic image 86 is simultaneously uploaded to the PACS 20 of the first medical institute 16, also at this time the universal interface software will assign an accession number to the patient diagnostic image 86 and coordinate the medical record number with the patient diagnostic image 86. Both the accession number and medical record number will be incorporated into the patient study. The accession number allows for all of the services and procedures, including the radiologist's written report to be billed under the assigned accession number. Then at an accessing step 60 the same physician or different physician uses one of the workstations 22, 22' at the first medical institute 16 to access the one or more patient diagnostic images 86 located on the PACS 20, which pertain to the patient. The physician reviews the at least one patient diagnostic image 86 and then prepares a written report using the dictaphone 46, keyboard 48, mouse 50 and monitors 38, 40, 56, 54, 52 described with regard to FIG. 2 above regarding the patient diagnostic image.

Figure 4:
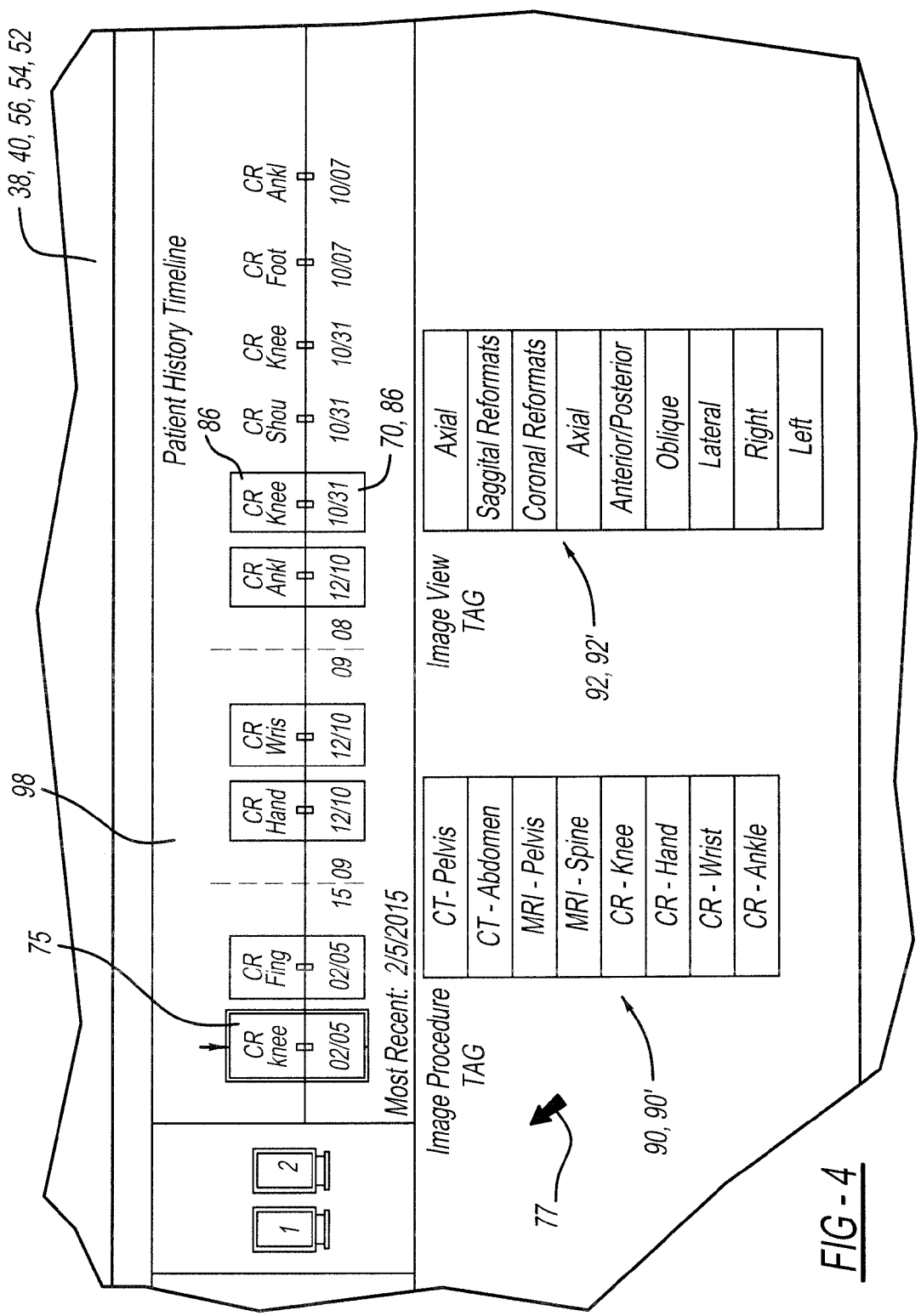
FIG. 4 is a screenshot of a patient history timeline, image procedure tag, and image view tag selection boxes.

Also referring to the screenshot shown in FIG. 4, a tagging step 62 occurs where the at least one diagnostic image is tagged by the physician or user of the workstation 22, 22' using a graphical user interface 77 to select at least one image procedure tag 90 pertaining to how the diagnostic image was obtained and at least one image view tag 92 pertaining to a viewpoint or location on the anatomy of the at least one diagnostic image 86. The tagging step 62 is carried out by the physician or user using the mouse 50 and drop-down menus presented on the first image monitor 38, second image monitor 40, voice recognition monitor 52, work list monitor 54, or cloud monitor 56 wherein a graphical user interface 77 is used to carry out the tagging step 62. Examples of different image procedure tags 90 include, but are not limited to the following types of diagnostic devices or modalities such as X-ray, CT scan, MRI, positron emission tomography (PET), mammograms (MG), computed radiography (CR) etc. Examples of image view tags 92 include but are not limited to the following axial, sagittal reformats, coronal reformats, anterior/posterior, lateral and oblique, right, left, etc. Next the universal interface software at an automatic sub-tagging step 64 will automatically assign anatomical sub-tags 94 that are based on the image procedure tag 90 and view tag 92 selected by the physician or user during the tagging step 62. The automatically assigned anatomical sub-tags 94 include but are not limited to the following anatomical sub-tags pertaining to the different portions of the anatomy that a particular image view and image procedure would also include such as thoracic, cranial, abdominal, pelvic, femur, tibia, spine, heart, lung, intestine, etc. For example a diagnostic image pertaining to the upper chest cavity focusing on the shoulder, would also be known to include portions of the heart, upper lung, ribs, cervical portion of the spinal column and possibly the lower mandible or jaw of the patient, each of which would be an anatomical sub-tag automatically tagged to the diagnostic image. This eliminates the need to have a user of the system log in all the anatomical sub-tags, which would be tedious and also depend on a user properly sub-tagging the image.

Generally the use of automatically assigned anatomical sub-tags 94, image view tags 92 and image procedure tags 90 in connection with each diagnostic image 86 that is part of a previous patient study 70 associates or tags words or terms with what is shown in the image. This makes it possible so that future searches of the patient library will be able to identify the diagnostic image and associated study by having tag words that match the search terms or words. Also using prepopulated image procedure tags, image view tags and automatically assigned sub-tags provides a common software nomenclature for all patient studies on the cloud server 12. The common nomenclature also assists users of the cloud server so they can accurately identify appropriate diagnostic images and previous patient studies for download and review. Search queries can be made to the cloud server 12 that will allow the universal interface software to quickly identify and retrieve relevant patient studies and patient diagnostic images from a particular patient's library stored on the cloud server. The common nomenclature focuses on the type of radiological diagnostic imaging device that took the patient image, the area of the human anatomy as well as many other factors such as angle and automatically assigned anatomical terms. Search queries made to the cloud server 12 can identify relevant images based on any of the aforementioned tags. Thus diagnostic images can be located on the cloud server that are specific to a specific type of diagnostic imaging device, or images and patient studies can be located based upon the view of the diagnostic image or even the anatomical sub-tags that are assigned by the universal interface software.

After the tagging step 62 and the automatic sub-tag assignment step 64 a patient study creation step 66 occurs where the written patient information or written report 96 prepared by the physician is saved into a file referred to as a previous patient study 70 that includes the patient name and date of the diagnostic images associated with the previous patient study 70. At a keyword tagging step 97 the universal interface software reads the written report and automatically generates keyword tags 93 by recognizing anatomical language in the written report. Then the universal interface software is used to complete the creation of the previous patient study 70 file so that it further includes the patient diagnostic image 86 or images, written report 96 pertaining to the patient diagnostic image 86, image procedure tags 90, image view tags 92, keyword tags 93, automatically assigned sub-tags 64 and the universal medical record number that is assigned by the universal interface software. The universal medical record number is a common number that will be used to identify the patient library 72 on the cloud server 12 and can be used among the different medical institutes for purposes of billing as well as keeping all of the individual patient images and patient study information within the patient library 72 on the cloud server 12. The medical record number is assigned by the universal interface software when the patient diagnostic image 86 is uploaded to the PACS at a final upload step 68.

During the final uploading step 68 the physician or other staff person at the medical institute using the workstation 22, 22' saves the patient study file to the PACS 20 at the first medical institute 16 and uploads the patient study file 70 to the cloud server 12 either from the PACS 20 or directly from the workstation 22, 22' as part of the final upload step 68. The patient study file 70, which is also referred to as a previous patient study file 70 is stored on the cloud server 12 in a patient library 72, which is contained within the data storage device 14 connected to the cloud server 12.

Creating at least one comparison diagnostic image step 74 occurs at the second medical institute 28 where a physician or user creates a comparison patient diagnostic image 75 of the patient (same patient as mentioned above with respect to the first medical institute 16). The comparison patient diagnostic image 75 is a single image, however there are typically several images that are prepared using the at least one radiological diagnostic image device 32. The at least one comparison patient diagnostic image 75 is uploaded from the at least one radiological diagnostic image device 32 to the PACS 30 of the second medical institute 28, also at this time the universal interface software will assign an accession number that coordinates with the PACS 30 to ensure reports are linked to the corresponding radiological images with subsequent billing for services. Also assigned is the medical record number relating to the patient diagnostic image 75 or images, which will be incorporated into the patient study. The medical record number is universal to the particular patient and will correlate to their patient library. The accession number also allows for all of the services and procedures, including the radiologist's written report to be billed under the assigned accession number. During an accessing step 76 the physician or user uses the workstation 34, 34' at second medical institute 28 to access the at least one comparison patient diagnostic image 75 located on the PACS 30 at the second medical institute 28.

Referring also to FIG. 4 a step of tagging 78 occurs, which is similar to the tagging step 62 that takes place at the first medical institute 16, During tagging step 78 the at least one patient comparison diagnostic image 75 is tagged when a physician or user of the at least one workstation 34, 34', uses a graphical user interface 77 located on the first image monitor 38, second image monitor 40, voice recognition monitor 52, work list monitor 54 or cloud monitor 56; where the universal interface software displays selection windows where the physician or user selects at least one image procedure tag 90' pertaining to nature of the image and how it was obtained including the following types of diagnostic devices or modalities such as X-ray, CT scan, MRI, positron emission tomography (PET), mammograms (MG), computed radiography (CR) etc. It is within the scope of this invention for other image procedure tags to be listed. The universal interface software also displays a selection window that allows the physician or user to operate the graphical user interface 77 to select at least one image view tag 92' pertaining to the viewpoint of the at least one comparison patient diagnostic image 75, which can be for example axial, sagittal reformats, coronal reformats, anterior/posterior, lateral, oblique, right, left, etc.

Next at a step 80 the universal interface software automatically assigns anatomical sub-tags 94' to the at least one patient comparison diagnostic image 75 using the universal interface software. During the step 80 the universal interface software is programmed to assign the anatomical sub-tags based on the at least one image procedure tag 90' and the at least one image view tag 92' selected by the physician or user during the tagging step 78.

The anatomical sub-tags 94' are visible or invisible tags that are associated with each diagnostic image, which allow for an appropriate image to be queried by the cloud server 12 based on several parameters including, but not limited to the device that the image was created with, angle of the viewpoint, anatomical features shown in the image and other automatically associated data that a physician or user may or may not necessarily include in their own tagging of the image. For example if an image were to show the upper main body cavity a physician only reviewing the image for a problem in the area of the stomach organ might not necessarily tag the image as also showing portions of the organs nearby or any skeletal bones that are visible in the image. The universal interface software is programmed to automatically assign anatomical sub-tags 94' and will recognize or add tags to a particular image based on the universal interface software being programmed to assign those sub-tags from the inputs selected by the physician or user. In other words the automatically assigned anatomical sub-tags 94' help to automate the tagging process without completely depending on the physician or user selecting all the appropriate tags, which can be cumbersome and also leave room for error.

With regard to the image procedure tags and image view tags at the first medical institute 16 and second medical institute 28, the at least one image procedure tag 90, 90' and the at least one image view tag 92, 92' are selected from pre-populated fields that the user reviewing the diagnostic image selects prior to uploading the image onto the cloud server 12. This allows for the universal interface software to then automatically assign anatomical sub-tags 94,94' based on the at least one image procedure tag and the at least one image view tag. The automatically assigned anatomical sub-tags 94, 94' the at least one image procedure tag 90, 90' and the at least one image view tag 92, 92' become part of the patient study, which allows for the patient library 72 on the cloud server 12 to be automatically searched so that a user of the cloud server 12 can quickly and seamlessly locate and view specific patient diagnostic images based on what the image shows and not necessarily based upon the type of image or vice versa. For example a user of the cloud server can search the at least one patient library for images showing portions of the specific patient's upper chest cavity regardless of the type of image (i.e., x-ray, CT scan, MRI scan).

After the physician or user has tagged the at least one comparison patient diagnostic image 75 and the universal interface software has automatically assigned anatomical sub-tags 94', at a step 82 the physician reviews the at least one comparison patient diagnostic image 75 and performs a typical diagnostic imaging read where the physician will prepare a written report, which is typically dictated using the dictaphone 46, keyboard 48 and voice recognition monitor 52 portions of the work station 34, 34'.

Sometimes during the review step 82 the physician identifies an abnormality in the at least one comparison patient diagnostic image 75 that requires further investigation. Typically diagnostic images do not contain abnormalities that require further investigation, therefore at decision step 81 a decision is made whether further patient history review or further studies are needed. For a majority of images further patient history review may not be necessary, therefore if no further patient history review or further studies are needed at step 83 a second previous patient study 70' is prepared and uploaded to the cloud server 12 in a manner identical or similar to the preparation of the previous patient study 70 prepared at the first medical institute 16 described above. During step 83 a written report 96' is prepared based on the comparison diagnostic images 75 (now considered at least one patient diagnostic image 75'). Then at a keyword tagging step 97' the universal interface software reads the written report and automatically generates keyword tags 93' by recognizing anatomical language in the written report. Then the universal interface software is used to complete the creation of the previous patient study 70' file so that it further includes the patient diagnostic images 75' or images, written report 96' pertaining to the patient diagnostic images 75', image procedure tags 90', image view tags 92', keyword tags 93', automatically assigned sub-tags 94', a universal medical record number, and accession number that are assigned by the universal interface software. At step 100 the previous patient study 70' is uploaded to the cloud server 12.

If at step 81 an abnormality is found then further investigation is typically needed. Typically further investigation involves taking further diagnostic images and performing additional patient studies, even for abnormalities that might be somewhat minor. For example a patient might have a benign tumor or cyst that was noted at other medical institutes. However unless a medical institute has some type of documentation or point of reference additional studies are performed. The present invention provides the advantage that documentation and point of reference in the form of previous patient studies saved to the cloud server 12 are readily available to the physician and staff at the second medical institute 28.

Next during an accessing step 85 at least one patient diagnostic library 72 on the cloud server 12 is accessed using the at least one workstation 34, 34' at the second medical institute 28. In performing the accessing step 85 the physician will use the at least one workstation 34, 34' to send a request to the cloud server 12 to search the at least one patient library 72 for any at least one patient diagnostic image 86 and a previous patient study 70, which includes a written report, date of the at least one patient diagnostic image 86, patient name and other information. The at least one patient diagnostic image 86 is identified because it contains the same anatomical sub-tags as the at least one comparison patient diagnostic image 75. Next the matching at least one patient diagnostic image 86 and its accompanying previous patient study 70 are downloaded from the cloud server 12 to the PACS 30 or workstation 34, 34' of the second medical institute 28. After downloading the patient diagnostic image 86 and the previous patient study 70 a physician can optionally perform a review step 108 (FIG. 8B) which is a decision box that requests the physician to decide whether to submit an official or nonofficial communication of the previous patient study 70. If the physician performs review step 108 then the universal interface software will ask whether the review will be an official review at decision box 110. If at decision box 110 an official review is to be conducted then an official review step 112 will take place and the official review will be submitted to the first medical institute 16 and or the patient library 72 on the cloud server 12.

Figure 6:
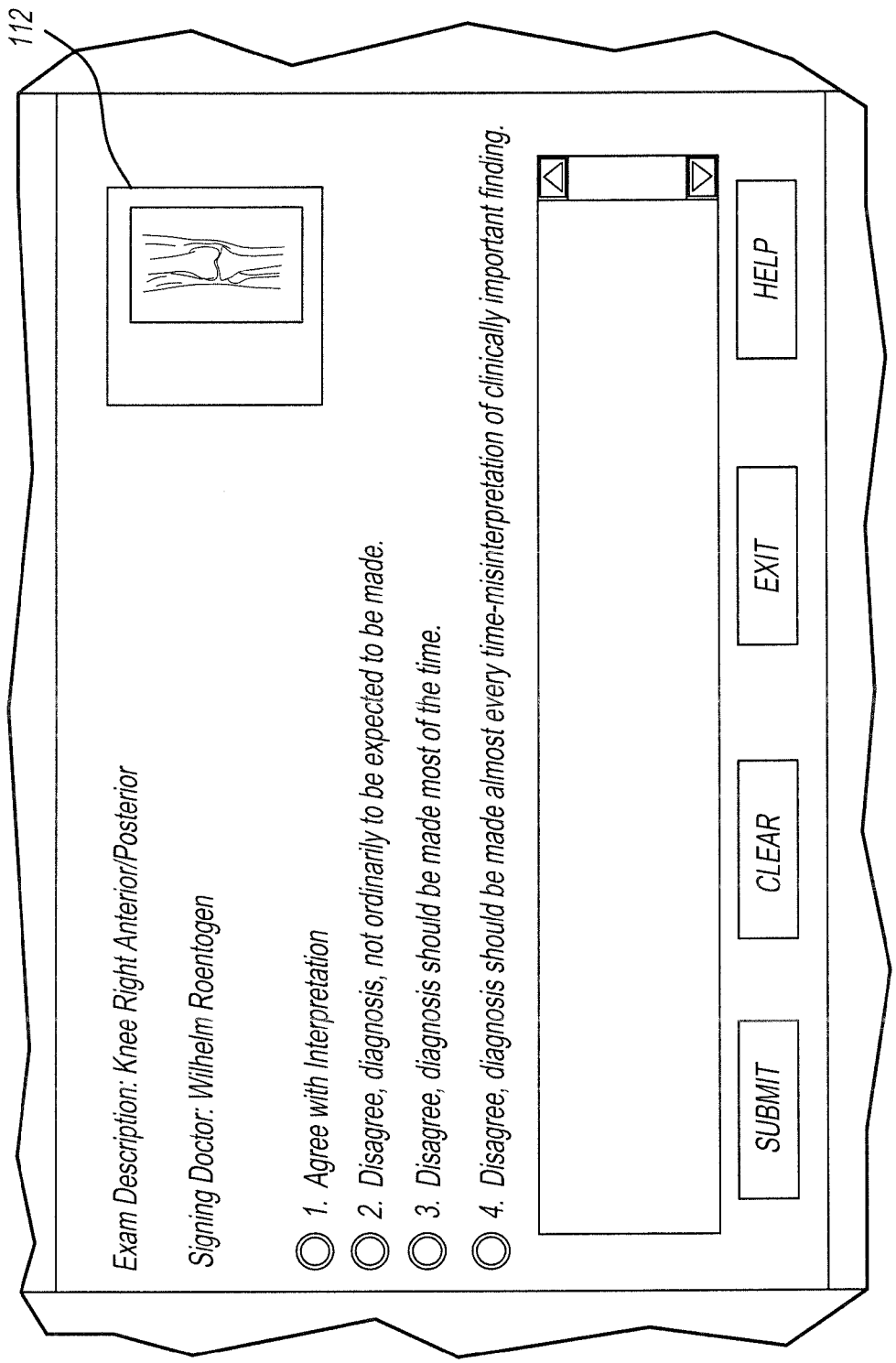
FIG. 6 is a screenshot of a sample official review window.

Referring now to FIG. 6 is a screenshot of an official review form where the physician may decide whether to agree or disagree with the conclusions of the previous patient study 70. There is also a text box where comments can be added and an image attachment portion where the image preview or thumbnail is visible. If at decision box 110 it is decided that an official review is not needed then at a non-official communication step 114 the physician may send the first medical institute or a physician at the first medical institute 16 an informal email or non-official communication 39, as show in in FIG. 1. A non-official communication step is sometimes more appropriate and helpful if the physician at the second medical institute 28 has some simple questions about the previous patient study, without necessarily agreeing or disagreeing with the results of the previous patient study. The non-official communication step 114 is also helpful for informal communications independent of the previous patient study 70, for example if the physician at the second medical institute 28 knows the signing physician at the first medical institute 16 and is seeking to simply send a personal message then the non-official communication step 114 would allow for such a communication.

If no review step 108 takes place or after the review step occurs, the next step is a create comparison patient study step 87 where the physician creates a comparison patient study 95 with a written report 96" comparing the at least one comparison patient diagnostic image 75 and the at least one patient diagnostic image 86 including the previous patient study 70 downloaded from the cloud server 12. The create comparison patient study step 87 will also include a review of the abnormality noted during the review step 82. Once the comparison patient study 95 has been prepared at a keyword tagging step 97, the universal interface software reads the written report 96" and automatically generates keyword tags 93" by recognizing anatomical language in the written report. At an uploading step 102 the comparison patient study 95 is uploaded to the PACS 30 at the second medical institute. Also at the uploading step 102 the comparison patient study is uploaded from the second medical institute 28 to the cloud server 12, which can originate from either the workstations 34, 34' or from the PACS 30.

Figure 5:
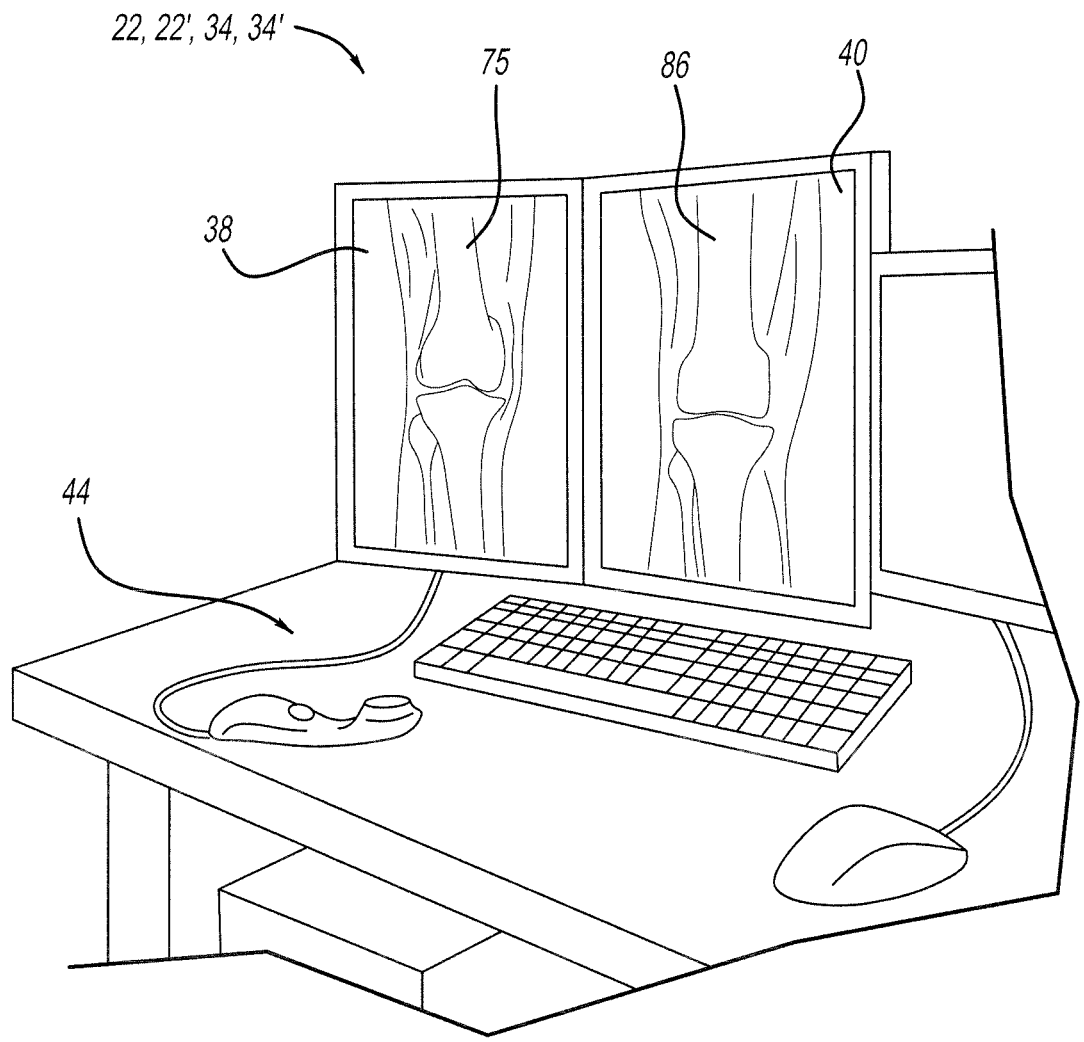
FIG. 5 is a front perspective view of the first image monitor and second image monitor, with various interface devices of the workstation.

Referring also to FIG. 5, during the create comparison patient study step 87 in FIG. 8B, the comparison patient study 95 is prepared using the first image monitor 38 and second image monitor 40 where the previous patient diagnostic image 86 or comparison diagnostic image 75 are displayed on one of the first image monitor 38 or second image monitor 40. On the first image monitor 38 or second image monitor 40 the at least one patient diagnostic image from the previous patient study is displayed so that a side-by-side comparison of the two images occurs.

FIG. 4 shows a timeline 98 is automatically created by the universal interface software, wherein the timeline 98 arranges the date of the comparison diagnostic image 75 or images and the date of the previous patient diagnostic image 86 or images from the previous patient study 70 into the timeline 98. At times there may be several previous patient studies 70 with multiple images that are downloaded from the cloud server 12, therefore the timeline 98 will help assist the physician in keeping the various diagnostic images organized when carrying out the comparison step and displaying the images side-by-side on the first image monitor 38 and second image monitor 40. The timeline 98 can be displayed on any one of the first image monitor 38, second image monitor 40, voice recognition monitor 52, worklist monitor 54 and cloud monitor 56. It is preferable the timeline be displayed on the worklist monitor 54 or cloud monitor 56.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for creating more comprehensive radiological reports and method of generating reports comprising:

providing a medical institute having radiological diagnostic image devices that include one or more of ultrasound, computed tomography (CT) scan, magnetic resonance imaging (MRI), positron emission tomography (PET), mammograms (MG), computed radiography (CR), nuclear medicine imaging and dual energy X-ray absorptiometry, workstations and a picture archiving and communication system (PACS) for creating a patient library and storing comparison patient diagnostic images and a previous patient study containing patient diagnostic images created or downloaded for review at the medical institute, wherein each one of the workstations includes a first image monitor and a second image monitor both having high resolution, wherein the first image monitor and the second image monitor are arranged in a side by side manner in order to assist the physician in comparing the comparison patient diagnostic images and the patient diagnostic images;

providing a universal interface software operating on PACS and accessible from the workstations for communicating between the workstations and PACS at the medical institute and for standardizing all information uploaded to PACS, the universal interface software interfaces between PACS and the workstations to send a request PACS to search the patient library and retrieve the previous patient study containing patient diagnostic images that have the same automatically assigned anatomical sub-tags as automatically assigned anatomical sub-tags of comparison patient diagnostic images;

providing image procedure tags created by the universal interface software, where the image procedure tags relate to how the patient diagnostic images or comparison patient diagnostic images were obtained and include the type of radiological diagnostic image device or modalities used;

providing image view tags created by the universal interface software, where the image view tags relate to the viewpoint of the patient diagnostic images or comparison patient diagnostic images;

providing the automatically assigned anatomical sub-tags generated by the universal interface software based on the combination of the image procedure tags and the image view tags, wherein the automatically assigned anatomical sub-tags relate to the different portions of the anatomy defined by the image procedure tags and the image view tags;

providing keyword tags generated by the universal interface software when the universal interface software reads a written report in the previous patient study or a written report in a comparison patient study where the universal interface software automatically generates the keyword tags by recognizing anatomical language in a written report of the previous patient study or a written report of a comparison patient study;

wherein the PACS stores the patient library using a format created by the universal interface software, thereby allowing the universal interface software to search the patient library stored on the PACS for the previous patient study that includes written patient information including patient name and date of study, the patient diagnostic images, the written report pertaining to the patient diagnostic images, image procedure tags pertaining to how the patient diagnostic images were obtained, the image view tags pertaining to the viewpoint of the patient diagnostic images, an automatically assigned universal medical record number associated with the previous patient study, and automatically assigned anatomical sub-tags;

creating at the medical institute the comparison patient diagnostic images of the patient using the radiological diagnostic image devices and uploading the comparison patient diagnostic images to the PACS at the medical institute;

using one of the workstations at the medical institute to access the comparison patient diagnostic images located on the picture archiving and communication system at the medical institute, tagging the patient comparison diagnostic images by a user of the one of the workstations at the second medical institute using a graphical user interface and the universal interface software to select the image procedure tags pertaining to how the comparison patient diagnostic images were obtained and the image view tags, wherein the image view tags pertain to the viewpoint of the patient diagnostic images;

automatically assigning with the universal interface software, the automatically assigned anatomical sub-tags and a universal medical record number to the comparison patient diagnostic images, wherein the image procedure tags, the image view tags and the automatically assigned anatomical sub-tags selected during the step of tagging are prepopulated to provide a common software nomenclature;

reviewing by a user the comparison patient diagnostic images and identifying an abnormality in the comparison patient diagnostic images that require further investigation;

accessing by the user using the one of the workstations and using the universal interface software to send a search request to the PACS to search the patient library for any patient diagnostic images containing the same said automatically assigned anatomical sub-tags as the comparison patient diagnostic images and downloading from the PACS to the one of the workstations the previous patient study and patient diagnostic images matching the search request;

using the universal interface software to automatically link the universal medical record number from the previous patient study to the universal medical record number of the comparison patient study;

creating the comparison patient study including a written report, prepared by the user, comparing the comparison patient diagnostic images and the previous patient study including the patient diagnostic images downloaded from the PACS, wherein the written report becomes part of said comparison patient study and includes a review of the abnormality noted in the comparison patient diagnostic images and the presence or absence of the abnormality in the previous patient study and the patient diagnostic images downloaded from the PACS;

performing a keyword tagging step wherein the universal interface software reads the written report and automatically generates keyword tags by recognizing anatomical language in the written report of the comparison patient study, wherein the keyword tags become part of the comparison patient study; and uploading the comparison patient study to the patient library on the PACS using the universal interface software.

2. The system of claim 1 wherein the step of creating the comparison patient study further includes organizing the patient diagnostic images from the previous patient study downloaded from the PACS and the comparison patient diagnostic images into a timeline on the one of the workstations of the medical institute, where said patient diagnostic images and the comparison diagnostic images are reviewed in a side by side comparison to conduct further investigation of the abnormality noted in the comparison patient diagnostic images.

3. The system of claim 1 further comprising the step of:
choosing between an official peer review of previous patient study downloaded from the PACS as part of the comparison study or a non-official communication.

4. The system of claim 3 further comprising the steps of:
selecting an official peer review;
accessing the written report of the previous patient study downloaded from the PACS and drafting a second written report regarding the findings of the patient, which includes physician contact information.

5. The system of claim 3 further comprising the steps of:
selecting non-official communication;
opening a communication screen used for contacting a physician that performed the previous patient study, wherein the communication screen is not documented in the previous patient study and does not constitute an official written report.

6. The system of claim 1 further comprising the steps of:
providing the patient with access to the patient library using a personal computer connected to the PACS and allowing a user of the personal computer to upload previous radiological images in their possession into the patient library.

7. The system of claim 1 further comprising the steps of:
providing a compact disc containing a manual patient study that includes written patient information including patient name and date of study, the manual patient study file includes patient diagnostic images;
loading the manual patient study from the compact disc onto the workstations at the medical institute, wherein the manual patient study is viewed on the one of the workstations;
creating a second opinion study file using the one of the workstations at the second medical institute, wherein the second opinion study file includes patient name, date of second opinion study, all information from the manual patient study and patient diagnostic images from the manual patient study;
viewing the patient diagnostic images from the manual patient study tagging the patient diagnostic images from the manual patient study by a user of the one of the workstations, using a graphical user interface and the universal interface software to select the image procedure tags pertaining to how the diagnostic images from the manual patient study was obtained;
automatically assigning anatomical sub-tags and a universal accession number to said patient diagnostic images from the manual patient study, wherein said universal interface software is programmed to assign the anatomical sub-tags based on the image procedure tags and the image view tags;
reviewing the patient diagnostic images from the manual patient study and preparing a written report that will become part of the second opinion study file prepared by a user after reviewing the patient diagnostic images from the manual patient study;

saving the second opinion study onto PACS at the medical Institute.

8. A system for creating more comprehensive radiological reports and method of generating reports comprising:

providing a medical institute having radiological diagnostic image devices that include one or more of X-ray radiograph, computed tomography (CT) scan, magnetic resonance imaging (MRI), positron emission tomography (PET), mammograms (MG), computed radiography (CR), workstations and a picture archiving and communication system (PACS) for creating a patient library and storing comparison patient diagnostic images and a previous patient study containing patient diagnostic images created or downloaded for review at the medical institute, wherein each one of the workstations includes a first image monitor and a second image monitor both having high resolution, wherein the first image monitor and the second image monitor are arranged in a side by side manner in order to assist the physician in comparing the comparison patient diagnostic images and the patient diagnostic images;

providing a universal interface software operating on PACS and accessible from the workstations for communicating between the workstations and PACS at the medical institute and for standardizing all information uploaded to PACS, the universal interface software interfaces between PACS and the workstations to send a request PACS to search the patient library and retrieve the previous patient study containing patient diagnostic images that have the same automatically assigned anatomical sub-tags as automatically assigned anatomical sub-tags of comparison patient diagnostic images;

providing image procedure tags created by the universal interface software, where the image procedure tags relate to how the patient diagnostic images or comparison patient diagnostic images were obtained and include the type of radiological diagnostic image device or modalities used;

providing image view tags created by the universal interface software, where the image view tags relate to the viewpoint of the patient diagnostic images or comparison patient diagnostic images;

providing the automatically assigned anatomical sub-tags generated by the universal interface software based on the combination of the image procedure tags and the image view tags, wherein the automatically assigned anatomical sub-tags relate to the different portions of the anatomy defined by the image procedure tags and the image view tags;

providing keyword tags generated by the universal interface software when the universal interface software reads a written report in the previous patient study or a written report in a comparison patient study where the universal interface software automatically generates the keyword tags by recognizing anatomical language in a written report of the previous patient study or a written report of a comparison patient study;

wherein the PACS stores the patient library using a format created by the universal interface software, thereby allowing the universal interface software to search the patient library stored on the PACS for the previous patient study that includes written patient information including patient name and date of study, the patient diagnostic images, the written report pertaining to the patient diagnostic images, image procedure tags pertaining to how the patient diagnostic images were obtained, the image view tags pertaining to the viewpoint of the patient diagnostic images, an automatically assigned universal medical record number associated with the previous patient study, and automatically assigned anatomical sub-tags;

creating at the medical institute the comparison patient diagnostic images of the patient using the radiological diagnostic image devices and uploading the comparison patient diagnostic images to the PACS at the medical institute;

using one of the workstations at the medical institute to access the comparison patient diagnostic images located on the picture archiving and communication system at the medical institute, tagging the patient comparison diagnostic images by a user of the one of the workstations at the second medical institute using a graphical user interface and the universal interface software to select the image procedure tags pertaining to how the comparison patient diagnostic images were obtained and the image view tags, wherein the image view tags pertain to the viewpoint of the patient diagnostic images;

automatically assigning with the universal interface software, the automatically assigned anatomical sub-tags and a universal medical record number to the comparison patient diagnostic images, wherein the image procedure tags, the image view tags and the automatically assigned anatomical sub-tags selected during the step of tagging are prepopulated to provide a common software nomenclature;

reviewing by a user the comparison patient diagnostic images and identifying an abnormality in the comparison patient diagnostic images that require further investigation;

accessing by the user using the one of the workstations and using the universal interface software to send a search request to the PACS to search the patient library for any patient diagnostic images containing the same said automatically assigned anatomical sub-tags as the comparison patient diagnostic images and downloading from the PACS to the one of the workstations the previous patient study and patient diagnostic images matching the search request;

using the universal interface software to automatically link the universal medical record number from the previous patient study to the universal medical record number of the comparison patient study;

creating the comparison patient study including a written report, prepared by the user, comparing the comparison patient diagnostic images and the previous patient study including the patient diagnostic images downloaded from the PACS, wherein the written report becomes part of said comparison patient study and includes a review of the abnormality noted in the comparison patient diagnostic images and the presence or absence of the abnormality in the previous patient study and the patient diagnostic images downloaded from the PACS;

performing a keyword tagging step wherein the universal interface software reads the written report and automatically generates keyword tags by recognizing anatomical language in the written report of the comparison patient study, wherein the keyword tags become part of the comparison patient study;

accessing the PACS and choosing between an official peer review of the previous patient study as part of the comparison study or a non-official communication; and uploading the comparison patient study to the patient library on the PACS using the universal interface software.

9. The system of claim 8 further comprising the steps of:
selecting non-official communication;
opening a communication screen used for contacting the physician that performed the previous patient study, wherein the communication screen is not documented in the previous patient study and does not constitute an official written report.

10. The system of claim 8 wherein the step of creating the comparison patient study further includes organizing the patient diagnostic images from the previous patient study downloaded from the PACS and the comparison patient diagnostic images into a timeline on the one of the workstations of the medical institute, where said patient diagnostic images and the comparison diagnostic images are reviewed in a side by side comparison to conduct further investigation of the abnormality noted in the comparison patient diagnostic images.

11. The system of claim 8 further comprising the steps of:
providing the patient with access to the patient library using a personal computer connected to the PACS and allowing a user of the personal computer to upload previous radiological images in their possession into the patient library.

12. The system of claim 8 further comprising the steps of:
providing a compact disc containing a manual patient study that includes written patient information including patient name and date of study, the manual patient study file includes patient diagnostic images;
loading the manual patient study from the compact disc onto the workstations at the medical institute, wherein the manual patient study is viewed on the one of the workstations;
creating a second opinion study file using the one of the workstations at the second medical institute, wherein the second opinion study file includes patient name, date of second opinion study, all information from the manual patient study and patient diagnostic images from the manual patient study;
viewing the patient diagnostic images from the manual patient study tagging the patient diagnostic images from the manual patient study by a user of the one of the workstations, using a graphical user interface and the universal interface software to select the image procedure tags pertaining to how the diagnostic images from the manual patient study was obtained;
automatically assigning anatomical sub-tags and a universal accession number to said patient diagnostic images from the manual patient study, wherein said universal interface software is programmed to assign the anatomical sub-tags based on the image procedure tags and the image view tags;
reviewing the patient diagnostic images from the manual patient study and preparing a written report that will become part of the second opinion study file prepared by a user after reviewing the patient diagnostic images from the manual patient study;
saving the second opinion study onto PACS at the medical Institute.

* * * * *